(12) United States Patent
Sorensen

(10) Patent No.: US 8,388,938 B2
(45) Date of Patent: Mar. 5, 2013

(54) SOLID ORAL TOOTH WHITENING CONFECTIONARY COMPOSITION

(75) Inventor: Edith Sorensen, Horsens (DK)

(73) Assignee: Cadbury Holdings Limited, Middlesex (GB)

( * ) Notice: Subject to any disclaimer, the term of this patent is extended or adjusted under 35 U.S.C. 154(b) by 1731 days.

(21) Appl. No.: 10/582,079

(22) PCT Filed: Dec. 8, 2004

(86) PCT No.: PCT/EP2004/013963
§ 371 (c)(1),
(2), (4) Date: Aug. 1, 2006

(87) PCT Pub. No.: WO2005/058264
PCT Pub. Date: Jun. 30, 2005

(65) Prior Publication Data
US 2007/0190086 A1 Aug. 16, 2007

Related U.S. Application Data

(63) Continuation-in-part of application No. PCT/EP03/13873, filed on Dec. 8, 2003.

(51) Int. Cl.
*A61Q 11/00* (2006.01)

(52) U.S. Cl. ............ 424/57; 424/401; 424/440; 424/464

(58) Field of Classification Search .................. None
See application file for complete search history.

(56) References Cited

U.S. PATENT DOCUMENTS

| | | | |
|---|---|---|---|
| 2,876,167 A | 3/1959 | Roderick | |
| 3,511,914 A * | 5/1970 | Wolkoff et al. | ............... 514/772 |
| 3,590,120 A | 6/1971 | Muhler | |
| 3,897,548 A | 7/1975 | Katz | |
| 3,928,618 A * | 12/1975 | Bauman | ........................ 514/551 |
| 3,957,967 A | 5/1976 | L'Orange | |
| 3,989,814 A | 11/1976 | Cordon et al. | |
| 4,170,633 A | 10/1979 | Wagenknecht et al. | |
| 4,233,288 A | 11/1980 | Cornell | |
| 4,400,372 A | 8/1983 | Muhler et al. | |
| 4,627,977 A | 12/1986 | Gaffar et al. | |
| 4,765,984 A * | 8/1988 | Vellekoop et al. | ............ 424/441 |
| 4,806,340 A | 2/1989 | Gaffar et al. | |
| 4,891,211 A | 1/1990 | Winston | |
| 4,975,270 A | 12/1990 | Kehoe | |
| 5,079,868 A * | 1/1992 | Hashimoto | ........................ 47/2 |
| 5,147,632 A | 9/1992 | Pan et al. | |
| 5,156,845 A * | 10/1992 | Grodberg | ...................... 424/440 |
| 5,470,566 A | 11/1995 | Lutzen | |

(Continued)

FOREIGN PATENT DOCUMENTS

| | | |
|---|---|---|
| DE | 3945147 | 3/1987 |
| EP | 0236290 | 9/1987 |

(Continued)

OTHER PUBLICATIONS

Partial machine translation of JP 01-172315 provided by Applicant. Published Jul. 7, 1989.*

(Continued)

*Primary Examiner* — Daniel Sullivan
*Assistant Examiner* — Barbara Frazier
(74) *Attorney, Agent, or Firm* — Greenblum & Bernstein, P.L.C.

(57) ABSTRACT

The present invention provides a solid, oral tooth whitening confectionary composition comprising a tooth whitening agent comprising an alkaline or alkaline earth metal pyrophosphate, preferably calcium pyrophosphate. In one embodiment, the composition of the invention comprises an additional tooth whitening agent.

25 Claims, 1 Drawing Sheet

U.S. PATENT DOCUMENTS

| | | | |
|---|---|---|---|
| 5,496,541 | A | 3/1996 | Cutler |
| 5,851,514 | A | 12/1998 | Hassan et al. |
| 5,861,169 | A | 1/1999 | Kaufmann |
| 6,174,516 | B1 | 1/2001 | Curtis et al. |
| 6,294,154 | B1 | 9/2001 | Hughes |
| 6,294,155 | B1 | 9/2001 | Thomas et al. |
| 6,331,291 | B1 | 12/2001 | Glace et al. |
| 6,350,438 | B1 * | 2/2002 | Witt et al. ............ 424/53 |
| 6,355,229 | B1 | 3/2002 | Adamy |
| 6,416,744 | B1 | 7/2002 | Robinson et al. |
| 6,500,406 | B1 | 12/2002 | Rajaiah et al. |
| 6,682,722 | B2 * | 1/2004 | Majeti et al. .......... 424/53 |
| 6,685,916 | B1 * | 2/2004 | Holme et al. .......... 424/48 |
| 6,703,000 | B2 * | 3/2004 | Ning et al. ............ 424/58 |
| 6,926,916 | B1 | 8/2005 | Day et al. |
| 2002/0061282 | A1 * | 5/2002 | Georgiades ........... 424/49 |
| 2002/0142068 | A1 | 10/2002 | Savage et al. |
| 2002/0187108 | A1 | 12/2002 | Rajaiah et al. |
| 2003/0068282 | A1 | 4/2003 | Green et al. |
| 2003/0068283 | A1 | 4/2003 | Cromwell et al. |
| 2003/0072722 | A1 | 4/2003 | Nathoo |
| 2003/0072841 | A1 | 4/2003 | Rajaiah et al. |
| 2003/0077232 | A1 | 4/2003 | Cromwell et al. |
| 2003/0082112 | A1 | 5/2003 | Hall et al. |
| 2003/0082113 | A1 | 5/2003 | Rajaiah et al. |
| 2003/0086878 | A1 | 5/2003 | Rajaiah et al. |
| 2003/0099740 | A1 | 5/2003 | Colle et al. |
| 2005/0019276 | A1 | 1/2005 | Nathoo |
| 2007/0081950 | A1 | 4/2007 | Sorensen |

FOREIGN PATENT DOCUMENTS

| | | |
|---|---|---|
| EP | 0309414 | 8/1988 |
| EP | 0288909 | 11/1988 |
| EP | 0372603 | 6/1990 |
| GB | 1018665 | 1/1966 |
| GB | 234870 | 10/2000 |
| JP | 61-180710 | 8/1986 |
| JP | 1-172315 | 7/1989 |
| WO | 86/06625 | 11/1986 |
| WO | 96/19190 | 6/1996 |
| WO | 97/11675 | 4/1997 |
| WO | WO 97/19668 * | 7/1997 |
| WO | 99/12517 | 3/1999 |
| WO | 00/25598 | 5/2000 |
| WO | 00/57842 | 10/2000 |
| WO | 01/56399 | 8/2001 |
| WO | 02/19834 | 3/2002 |
| WO | 02/074409 | 9/2002 |
| WO | 03/002056 | 1/2003 |
| WO | 03/017964 | 3/2003 |
| WO | 2005/058263 | 6/2005 |

OTHER PUBLICATIONS

Translation of WO 97/19668.*
Elmore, "Final Report on the Safety Assessment of Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth, Hectorite, Kaolin, Lithium Magnesium Silicate, Lithium Magnesium Sodium Silicate, Montmorillonite, Pyrophyllite, and Zeolite", International Journal of Toxicology, 22(Suppl. 1):37-1-2, 2003.
FDA, U.S. Food and Drug Administration, Title 21, vol. 3, Revised as of Apr. 1, 2007, 21 CFR 172.615 (7 pages).
Stookey et al., "In Vitro Removal of Stain with Dentifrices", J. Dent. Res., vol. 61, No. 11, Nov. 1982, pp. 1236-1239.
Kleber et al., "A Mastification Device Designed for the Evaluation of Chewing Gums", J. Dent. Res., vol. 60, No. 2, Feb. 1981, pp. 109-114.
U.S. Appl. No. 10/582,223 to Sorensen, Edith filed Apr. 12, 2007.
U.S. Appl. No. 10/582,223 to Edith Sorensen et al., filed Jun. 8, 2006.
English Language Abstract of JP 1-172315.
English Language Abstract of JP 61-180710.
Machine English translation of JP 2580661B.
Gibbs et al., "Encapsulation in the food industry: a review.", International Journal of Food Sciences and Nutrition; 1999:50; 213-224.
Putt et al., "A comparison of the Polishing Properties of Human and Bovine Enamel", J Dent Res 1980:59(7); 1177.

* cited by examiner

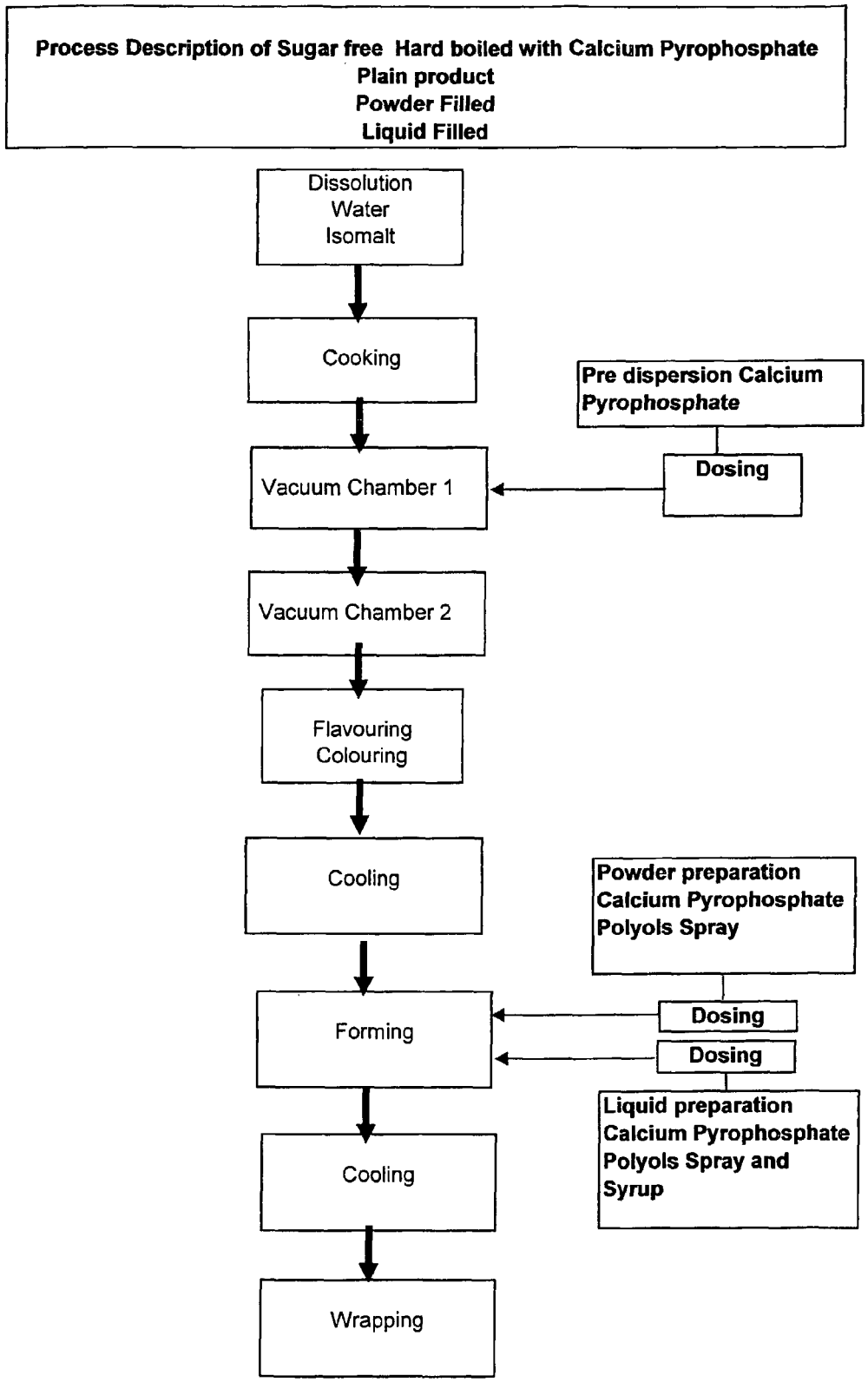

SOLID ORAL TOOTH WHITENING CONFECTIONARY COMPOSITION

CROSS-REFERENCE TO RELATED APPLICATIONS

This application is a National Stage Application of International Application No. PCT/EP2004/013963, filed Dec. 8, 2004, which is a Continuation-In-Part of International Application No. PCT/EP03/13873, filed Dec. 8, 2003.

TECHNICAL FIELD

The invention relates to solid, oral tooth whitening confectionary compositions. The invention further relates to the use of such compositions to whiten tooth surfaces.

BACKGROUND ART

Tooth whitening or stain removing agents are known to be added to dentifrice compositions such as toothpaste, mouthwash, chewing gum, confectionary compositions and the like. The use of such compositions for reducing stains and discolouration of tooth surfaces thereby improving the general cosmetic appearance of the teeth is likewise well-known. Teeth with extrinsic stains are objectionable both on the basis of cosmetic appearance and also socially as indication of poor oral hygiene.

Some products contain peroxides, but these are, however, problematic from a toxicological point of view. Another approach to tooth whitening products is to add abrasives—known mainly from dentifrices. Not all of these are legal in confectionary. Further, a significant tooth whitening effect would not be expected to occur following the consumption of confectionary compositions comprising abrasives as these compositions are not suitable for continuous chewing.

Several abrasive agents have been used for tooth whitening purposes and these are known to the person skilled in the art. Examples of abrasive agents include calcium carbonate, sodium bicarbonate, sodium metaphosphate, potassium metaphosphate, tricalcium phosphate, dihydrated dicalcium phosphate, calcium pyrophosphate, bentonite, zirconium silicate or other siliceous materials. Other suitable abrasives are described in U.S. Pat. No. 4,170,633 and U.S. Pat. No. 4,891,211, incorporated herein by reference.

Several patents and patent applications disclose the use of abrasive materials in solid, oral compositions, see for example U.S. Pat. Nos. 5,147,632 and 5,496,541, EP Patent No. 372,603, International Publication Nos. WO 02/19834 and WO 01/56399.

US Patent Application US 2002/0142068 discloses chewing gum formulations including sodium pyrophosphate and encapsulated aspartame.

U.S. Pat. No. 4,233,288 discloses a gum emulsified liquid composition for delivering and preserving the liquid content in the mouth. The herein disclosed examples describe a gum emulsified liquid composition comprising 5% of calcium pyrophosphate and more than 50% of liquid components.

U.S. Pat. No. 3,590,120 discloses a chewing gum comprising a polishing agent comprising a mixture of fine and coarse zirconium silicate particles. Disclosed herein are reference chewing gum compositions containing 10% of calcium pyrophosphate or 10% of calcium carbonate, respectively. The cleaning/polishing effects of said compositions are shown to decrease in the order $ZrSiO_4$, $CaCO_3$ and $CaP_2O_7$. Indicative studies have however shown some problematic toxicological properties of zirconium silicate (Elmore AR, Cosmetic Ingredient Review Expert Panel, Final report on the safety assessment of aluminum silicate, calcium silicate, magnesium aluminium silicate, magnesium silicate, magnesium trisilicate, sodium magnesium silicate, zirconium silicate, attapulgite, bentonite, Fuller's earth, hectorite, kaolin, lithium magnesium silicate, lithium magnesium sodium silicate, montmorillonite, pyrophyllite, and zeolite, Int. J Toxicol. 2003; 22 Suppl. 1:37-102) and the use of zirconium compounds in solid oral compositions is prohibited in a number of countries.

Thus, a need exists in the art to identify and use abrasives in solid, oral tooth whitening compositions, to obtain an increased whitening effect, which compositions are safe and convenient to administer and apply.

DISCLOSURE OF INVENTION

The present invention relates to a solid oral tooth whitening confectionary composition comprising more than 75% by weight of solid materials, said composition comprising:
  a) a confectionary base,
  b) conventional confectionary additives,
  c) a tooth whitening agent comprising an alkaline or alkaline earth metal pyrophosphate.

Furthermore, the present invention relates to the use of a composition according to the present invention to whiten tooth surfaces.

Furthermore, the present invention relates to a method of whitening tooth surfaces.

BRIEF DESCRIPTION OF DRAWING

The invention is explained in greater detail below with reference to the accompanying drawing, in which FIG. 1 is a diagrammatic view of the process for preparing hard-boiled lozenges as disclosed in example 1.

BEST MODES FOR CARRYING OUT THE INVENTION

In a preferred embodiment according to the present invention the solid oral tooth whitening confectionary composition comprises confectionary additives and a tooth whitening agent comprising calcium pyrophosphate.

The use of abrasives, among which calcium pyrophosphate is normally classified, in confectionary, would not be expected to cause a tooth whitening effect comparable to the effect when used in compositions intended for continuous chewing, i.e. chewing gum compositions, since confectionary compositions are not chewed to the same extent. As a consequence the stain removal effect of the abrasive material would be expected to be insignificant due to the minimal mechanical rubbing on the tooth surface.

It has now surprisingly been demonstrated, using in vitro tests, that improved stain removal effects of solid, oral confectionary compositions can be achieved using from 0.1 to 10% of calcium pyrophosphate as an abrasive agent, compared to the use of the often used abrasive, calcium carbonate.

These effects are further unexpected, seen in the light of the results presented in U.S. Pat. No. 3,590,120, in which the effect of $CaP_2O_7$ was significantly poorer than that of $CaCO_3$.

Typically, confectionary tooth whitening compositions are intended to comprise a recommended daily dose of tooth whitening agent of about 4 to 700 mg. Conveniently, this dose may be divided into multiple sub-doses, which can be ingested as needed such as at suitable intervals or in suitable situations, i.e. after meals, after use of substances known to induce stain formation, i.e. coffee, tea, red wine, tobacco and the like. Assuming a confectionary unit weight of 1300 mg, a content of 0.1% to 10% of tooth whitening agent corresponds to a composition unit content of approximately 1.3 to 130 mg of tooth whitening agent.

The compositions of the invention are essentially solid and comprise more than 75%, preferably more than 85%, even more preferably more than 95%, by weight of the composition of solid materials.

The solid material comprises a confectionary base, conventional confectionary additives and a tooth whitening agent.

In a preferred embodiment of the invention, calcium pyrophosphate is present in an amount of between 0.5% and 9%, preferably between 1.0% and 6.5%, even more preferably between 1.5% and 4.0%, by weight of the composition.

In a preferred embodiment, the compositions of the invention are formulated as confectionary compositions comprising a confectionary base, said confectionary base preferably comprising from 5% to 99%, particularly from 15% to 98%, preferably 30% to 97% by weight of the composition. Non-limiting examples of confectionary compositions according to the invention include hard-boiled, grained sugar confectionary, lozenges, chocolate, compressed tablets, gummy confectionary and jellies. Confectionary base materials are well known to the person skilled in the art and vary according to the type of confectionary composition, e.g. the compositions mentioned above.

The compositions according to the present invention may contain one or more conventional ingredients such as sweeteners, high intensity sweeteners, taste enhancers, flavouring agents and the like. Sweeteners, high intensity sweeteners and taste enhancers are well known to the skilled person. Non-limiting examples of sweeteners comprise sugar sweeteners including saccharides such as sucrose, dextrose, glucose, maltose, dextrins, D-tagatose, trehalose, dried invert sugar, fructose, levulose, galactose, corn syrup solids, and the like, alone or in combination. Other examples of sweeteners comprise sugarless sweeteners including polyhydric alcohols such as sorbitol, mannitol, xylitol, glycerol, hydrogenated starch hydrolysates, maltitol, isomaltitol, erythritol, lactitol and the like, alone or in combination. Sugarless sweeteners are preferred.

Preferred high intensity sweeteners include but are not limited to sucralose, aspartame, superaspartame, sucronic acid, Twinsweet™, neohesperidin dihydrochalcone, stevia, brazzein, mogroside, Monatin™, Ajinomoto™ sweetener, alapyridaine, tagatose, rebaudioside A, salts of acesulfame, alitame, saccharin or salts herof, neotame, cyclamic acid and salts thereof, glycyrrhizin, dihydrochalcones, thaumatin, monnelin, sterioside and the like, alone or in combination.

A variety of flavours known in the art may be used, such as cinnamon, wintergreen, eucalyptus, spearmint, peppermint, menthol, anise as well as fruit flavours such as apple, pear, peach, strawberry, cherry, apricot, orange, watermelon, banana and the like; bean-derived flavours, such as coffee, cocoa and the like. Flavouring agents are incorporated in the confectionary formulation at a concentration of about 0.1 to about 5% by weight and preferably 1 to 3% by weight.

The compositions of the invention may or may not contain sugar. Sugar-free compositions, however, are preferred.

It may be advantageous to include one or more additional tooth whitening agents.

Examples of such additional tooth whitening agents are well known in the art and include abrasives as well as bleaching agents. Abrasive materials comprise as non-limiting examples silica, alumina, calcium carbonate, dicalcium phosphate, hydroxyapatite, trimetaphosphates and insoluble hexametaphosphates. Bleaching agents comprise agents such as peroxy compounds, e.g. potassium peroxydiphosphate and urea-peroxid. Effervescing systems such as sodium bicarbonate, alone or in combination with citric acid as well as colour change systems may also be incorporated into compositions according to the present invention.

In the compositions according to the invention, said additional whitening agents are usually present in between 0.01% and 5.0%, preferably between 0.05 and 1.0%, more preferably between 0.1% and 0.5% by weight of the composition.

A preferred additional tooth whitening agent comprises a bicarbonate salt. In one embodiment, said bicarbonate salt comprises sodium bicarbonate in an amount of between 0.1% and 0.5% by weight of the compositions.

A range of active agents may be added to the compositions of the invention. Such agents may comprise one or more of the following; oral hygiene promoting agents, anti-calculus agents, anti-microbial agents, anti-inflammatory agents, desensitising agents, therapeutically active agents, remineralising agents. Non-limiting examples comprise anti-caries agents such as sodium, calcium, magnesium and stannous fluoride, amine fluorides, disodium monofluorophosphate, sodium trimetaphosphate and casein; antimicrobial agents, e.g. Triclosan, chlorhexidine, copper, zinc and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol); anti-inflammatory agents such as ibuprofen, flurbiprofen, aspirin, indomethacin etc.; plaque acid buffers such as urea, calcium lactate, calcium glycerophosphate and strontium polyacrylates; desensitising agents, e.g. potassium citrate, potassium chloride, potassium tartrate, potassium bicarbonate, potassium oxalate, potassium nitrate and strontium salts; anti-calculus agents, e.g. hypophosphite-containing polymers, organic phosphonates and phosphocitrates etc.; gum protection agents, e.g. vegetable oils such as sunflower oil, rape seed oil, soybean oil, safflower oil; silicone oil; and hydrocarbon oil; pharmaceutically acceptable carriers, e.g. starch, sucrose, water or water/alcohol systems etc.; surfactants, such as anionic, nonionic, cationic and zwitterionic or amphoteric surfactants. Other agents which may be incorporated in the compositions of the present invention are agents to counter breath malodour and include water soluble zinc salts (at least 1% soluble) particularly zinc chloride, zinc acetate, zinc citrate and zinc gluconate.

The additives, the whitening agents and the optional active agents comprised by the present invention may be encapsulated. This may be done in order to achieve a slow release of the encapsulated agents upon entering the oral environment. For example a longer lasting sweetening of the compounds comprised by the present invention may be achieved by encapsulating the sweetening agents. A longer release time of the whitening agents as well as any therapeutic compound may likewise be achieved.

Another advantage of encapsulating the agents comprised by the invention may be to obtain an increased stability of the agents, thus lending a longer storage life at a greater range of storage conditions to the compositions of the invention.

Any standard method giving partial or full encapsulation can be used for encapsulation. Suitable methods include, but are not limited to, spray drying, spray chilling, fluid-bed coating, and coacervation. These methods can be used individually or in any combination in a single step process or multiple step process.

Generally, compositions of high organic solubility, good film forming properties, and low water solubility, provide a suitable encapsulation. These compositions include acrylic polymers and copolymers, carboxyvinyl polymers, polyamides, polystyrene, polyvinyl acetate, polyvinyl acetate phthalate, polyvinyl pyrrolidone, and waxes.

However, only food grade materials should be used for the encapsulation. Two standard food grade coating materials, which are good formers, but not water soluble, are shellac and Zein. Others which are more water soluble, but also good film formers, are materials such as agar, alginates, a wide range of cellulose derivatives like ethyl cellulose and hydroxypropylmethyl cellulose, dextrin, gelatin and modified starches. It is also possible to use other encapsulants like acacia or maltodextrin for encapsulation.

In yet another embodiment of the invention, it may be desirable to include a supplement, such as vitamins and/or minerals in the composition according to the invention. Vitamins are preferably added in concentrations of between 10%-100% of the recommended daily allowance (RDA).

Especially vitamin C may be added to the compositions of the invention.

It may be desirable to include urea in the compositions of the invention. Urea may be added as a plaque acid neutralising agent. Usually urea is added to the compositions in between 0.1% and 25%, particularly between 0.4% and 10%, preferably between 0.6% and 5.0%, more preferably between 0.7% and 3.5%, even more preferably between 0.8% and 2.5% by weight.

The compositions according to the invention may be in the form of lozenges. In a particularly embodiment of the invention said lozenges are hard-boiled lozenges. Lozenges may be prepared according to conventional procedures as disclosed in more detail in the examples below. Thus compositions according to the invention in the form of lozenges may be in the form of plain lozenges, wherein all ingredients are mixed more or less homogenously. Furthermore the compositions according to the invention may be in the form of lozenges having either a powder-filled or a liquid-filled centre.

In another embodiment, the present invention relates to the use of the compositions of the invention to whiten tooth surfaces and/or prevent discolouration of tooth surfaces. Especially, the compositions of the invention may be used to remove or prevent discolouration of teeth due to the use of tobacco-related products and/or consumption of red wine or related products as well as coffee, tea or related products.

EXAMPLES

Example 1

Manufacture of sugar-free hard-boiled compositions containing calcium pyrophosphate The manufacturing process is diagrammatically shown in FIG. 1.

Base Composition:

| Water content | 2% |
|---|---|
| Isomalt | 98% |
| Acesulfame K | 0.05% |
| Flavours/Colours | QS |

A confectionary base containing 98% isomalt, 0.05% acesulfame K and approx. 2% water was prepared by dissolving isomalt and acesulfame K in water followed by cooking. The mixture was thereafter placed under vacuum. Colouring agents and flavouring agents are added after vacuum treatment. Optionally several vacuum chambers can be used. The composition was subsequently cooled until the composition reached a temperature suitable to form the desired confectionary pieces. Thereafter it was formed and subjected to a final cooling step.

Composition 1—Plain Sweet:

| Water content | 2% |
|---|---|
| Isomalt | 92% |
| Polyol syrup | 4% |
| Calcium pyrophosphate | 2% |
| Acesulfame K | 0.05% |

Calcium pyrophosphate in an amount corresponding to 2% of the total composition was added to the above confectionary base together with a polyol syrup (4% of total). Addition was done after the cooking of the confectionary base during the vacuum process.

Composition 2—Powder-Filled:

| Powder Filling recipe | |
|---|---|
| Polyols spray | 70% |
| Calcium Pyrophosphate | 30% |
| Flavours Colours | QS |
| Total recipe | |
| Base SF Hard Boiled | 93.3% |
| Powder filling | 6.7% |

A powder-filled confectionary composition was prepared by adding a total of 6.7% of a powder comprising 30% calcium pyrophosphate and 70% of a polyol spray to 93.3% of the base confectionary composition during the forming step in the above procedure. The final composition contained approx. 2% calcium pyrophosphate.

Composition 3—Liquid-Filled:

| Liquid Filling | |
|---|---|
| Water Content | 10% |
| Polyols spray | 50% |
| Polyols syrup | 26% |
| Calcium Pyrophosphate | 14% |
| Flavours Colours | QS |
| Total recipe | |
| Base SF Hard Boiled | 85% |
| Powder filling | 15% |

A liquid-filled confectionary composition was prepared by adding a total of 15% of a liquid comprising 14% calcium pyrophosphate, 50% of a polyol spray, 26% of a polyol syrup and 10% water to 85% of the base confectionary composition during the forming step in the above procedure. The final composition contained approx. 2% calcium pyrophosphate Example 2

The effect of solid oral tooth whitening confectionary compositions on the removal of extrinsic stains from teeth after 60 minutes treatment.

In the following non-limiting example, the inventive confectionary compositions are formulated as standard lozenge compositions, wherein the sweeteners constitute the confectionary base. In addition to the specified tooth whitening ingredients the standard lozenge compositions used herein consists essentially of the following ingredients:

| | |
|---|---|
| Isomalt | 96.22%–99.67% |
| Aspartame | 0.09% |
| Acesulfame K | 0.04%–0.05% |
| Xylitol | 0.00–1.29% |
| Menthol Flavour | 0.03%–0.04% |
| Lemon Flavour | 0.15% |

The above lozenge composition was prepared similar to the procedure of example 1, composition 1.

An assay for the effect of the tooth whitening compositions on the removal of extrinsic stains on tooth surfaces was set up. The assay consisted of treatments with five different lozenge compositions and a treatment with distilled water.

The lozenge compositions contained by weight of the composition the confectionary additives stated above, in addition to one of the following combinations;
1) 1.44% of calcium carbonate and 0.12% sodium bicarbonate ($CaCO_3$+Na—$HCO_3$),
2) 2.08% of calcium pyrophosphate and 0.12% sodium bicarbonate ($CaP_2O_7$+Na—$HCO_3$),
3) 0.12% sodium bicarbonate ($NaHCO_3$),
4) 2.08% of calcium pyrophosphate ($CaP_2O_7$),
5) No abrasive (negative control),
6) No lozenge (negative control, water).

The experiments were conducted using a modification of the laboratory method described by Stookey, G K: Burkhart, T. A: and Schemehorn, B. R; In vitro removal of stain with dentifrices, J Dent Res 61(11):1236-1239, November 1982, which has been shown to correlate with the cleaning/whitening properties of dentifrices in clinical trials. The amount of stain on the teeth before and after treatment is measured quantitatively using a colorimeter.

Each composition was tested on four enamel pieces containing a stained pellicle layer. The enamels pieces were stained with a broth comprising coffee, tea, red wine, gastric mucin as well as a culture of the micro-organism *Micrococcus luteus*. Prior to treatment the colour of the stained teeth was measured using a calorimeter, and 6 groups containing 4 teeth each balanced for baseline stains were formed.

The lozenge compositions were diluted 1 part by weight with 3 parts distilled water to simulate salivary dilution. 10 ml of lozenge test solution was placed in a beaker along with one of the stained teeth and mechanically stirred for 20 minutes. Each tooth received a total of 60 minutes treatment divided into three 20-minute treatments. Each new 20 minute treatment was carried out using fresh lozenge test solution.

After completion of treatments the stains remaining on the teeth were measured using a calorimeter. The before and after measurements were used to calculate the overall change in colour ($\Delta E$), based on the standard CIELAB colour procedure.

Hereafter teeth were cleaned completely using professional dental cleaning equipment, and another measurement using the colorimeter was done in order to determine the total amount of removable stain initially present on the teeth. A percent stain reduction was then calculated by dividing the amount of stain removed by the lozenge treatments by the total amount of removable stain.

The mean values and the standard deviations for each treatment group are shown in table 1, column 2 ($\Delta E$). The maximum removal and the concomitant standard deviations are shown in column 3 (Maximum $\Delta E$). The % of reduction of stains is shown in column 4 (Reduction).

The values in each column with the same superscript are not statistically different, while those with different superscript are different at $p<0.05$ based on ANOVA and SNK testing.

TABLE 1

| Composition | $\Delta E$ | Maximum $\Delta E$ | Reduction |
|---|---|---|---|
| 1 ($CaCO_3$ + Na—$HCO_3$) | $0.69 \pm 0.37^a$ | $27.58 \pm 2.12^a$ | $2.5\%^a$ |
| 2 ($CaP_2O_7$ + Na—$HCO_3$) | $2.83 \pm 0.67^b$ | $30.72 \pm 1.04^a$ | $9.2\%^b$ |
| 3 ($NaHCO_3$) | $0.70 \pm 0.12^a$ | $29.88 \pm 2.32^a$ | $2.3\%^a$ |
| 4 ($CaP_2O_7$) | $5.62 \pm 1.66^c$ | $31.56 \pm 3.57^a$ | $17.6\%^c$ |
| 5 (no abrasive) | $0.59 \pm 0.35^a$ | $28.59 \pm 0.66^a$ | $2.1\%^a$ |
| 6 (water) | $0.51 \pm 0.24^a$ | $30.63 \pm 3.40^a$ | $1.7\%^a$ |

The invention claimed is:

1. A solid oral tooth whitening lozenge composition comprising more than 75% by weight of solid materials, said composition comprising:
   a) a water-soluble lozenge base,
   b) lozenge additives, and
   c) a tooth whitening agent comprising calcium pyrophosphate, said calcium pyrophosphate is present in an amount of between 1.5% and 4.0% by weight of the composition.

2. The composition according to claim 1 wherein said lozenge additives comprise at least one of the following: sweeteners, high intensity sweeteners, taste enhancers, flavoring agents, coloring agents.

3. The composition according to claim 1 wherein said composition is sugar-free.

4. The composition according to claim 1 comprising at least one additional tooth whitening agent.

5. The composition according to claim 4 wherein said at least one additional tooth whitening agent is present in between 0.01% and 5.0% by weight of the composition.

6. The composition according to claim 4 wherein said at least one additional tooth whitening agent comprises a bicarbonate salt.

7. The composition according to claim 6 wherein said at least one additional tooth whitening agent comprises sodium bicarbonate, said agent being present in between 0.1% and 0.5% by weight of the composition.

8. The composition according to claim 1 wherein at least one of said additives and said tooth whitening agent is encapsulated.

9. The composition according to claim 1 further comprising at least one of the following: oral hygiene promoting agents, anti-calculus agents, anti-microbial agents, anti-inflammatory agents, desensitizing agents, therapeutically active agents, and reminineralizing agents.

10. The composition according to claim 1 further comprising a supplement.

11. The composition according to claim 10 wherein said supplement comprises vitamin C.

12. The composition according to claim 9 wherein said composition further comprises an oral hygiene promoting agent, and the oral hygiene promoting agent comprises urea, said urea being present in between 0.1% and 25% by weight of the composition.

13. The composition according to claim 1 in the form of hard-boiled lozenges.

14. A method whitening tooth surfaces comprises applying a composition according to claim 1 to tooth surfaces.

15. The method according to claim 14 wherein said tooth surfaces are discolored by red wine products.

16. The method according to claim 14 wherein said tooth surfaces are discolored by coffee products.

17. A method of whitening tooth surfaces by consuming a solid, oral tooth whitening lozenge composition according claim 1.

18. A method of whitening tooth surfaces by consuming a solid oral tooth whitening lozenge composition according to claim 1, said tooth surfaces being discolored after use of red wine products.

19. A method of whitening tooth surfaces by consuming a solid oral tooth whitening lozenge composition according to claim 1, said tooth surfaces being discolored after use of coffee products.

20. The composition according to claim 5 wherein said at least one additional tooth whitening agent is present in between 0.05 and 1.0% by weight of the composition.

21. The composition according to claim 5 wherein said at least one additional tooth whitening agent is present in between 0.1% and 0.5% by weight of the composition.

22. The composition according to claim 9 wherein said composition further comprises an oral hygiene promoting agent, and the oral hygiene promoting agent comprises urea, said urea being present in between 0.4% and 10% by weight of the composition.

23. The composition according to claim 9 wherein said composition further comprises an oral hygiene promoting agent, and the oral hygiene promoting agent comprises urea, said urea being present in between 0.6% and 5.0% by weight of the composition.

24. The composition according to claim 9 wherein said composition further comprises an oral hygiene promoting agent, and the oral hygiene promoting agent comprises urea, said urea being present in between 0.7% and 3.5% by weight of the composition.

25. The composition according to claim 9 wherein said composition further comprises an oral hygiene promoting agent, and the oral hygiene promoting agent comprises urea, said urea being present in between 0.8% and 2.5% by weight of the composition.

* * * * *